(12) United States Patent
Lightner et al.

(10) Patent No.: US 7,858,846 B2
(45) Date of Patent: Dec. 28, 2010

(54) GENERATION OF PLANTS WITH ALTERED OIL CONTENT

(75) Inventors: Jonathan Lightner, Des Moines, IA (US); John Davies, Portland, OR (US); Hein Tsoeng Ng, Beaverton, OR (US)

(73) Assignee: Agrigenetics Inc, Indianapolis, IN (US)

( * ) Notice: Subject to any disclaimer, the term of this patent is extended or adjusted under 35 U.S.C. 154(b) by 1104 days.

(21) Appl. No.: 11/578,894

(22) PCT Filed: Apr. 20, 2005

(86) PCT No.: PCT/US2005/013398

§ 371 (c)(1),
(2), (4) Date: Oct. 20, 2006

(87) PCT Pub. No.: WO2005/103268

PCT Pub. Date: Nov. 3, 2005

(65) Prior Publication Data

US 2008/0118622 A1    May 22, 2008

Related U.S. Application Data

(60) Provisional application No. 60/564,532, filed on Apr. 22, 2004.

(51) Int. Cl.
*C12N 15/82* (2006.01)
(52) U.S. Cl. .................................................. 800/281
(58) Field of Classification Search ...................... None
See application file for complete search history.

(56) References Cited

U.S. PATENT DOCUMENTS

| | | | |
|---|---|---|---|
| 5,639,790 A | 6/1997 | Voelker et al. | |
| 5,704,160 A | 1/1998 | Bergquist et al. | |
| 6,229,033 B1 | 5/2001 | Knowlton | |
| 6,248,939 B1 | 6/2001 | Leto et al. | |
| 2003/0101481 A1* | 5/2003 | Zhang et al. | 800/278 |
| 2004/0045049 A1 | 3/2004 | Zhang et al. | |

FOREIGN PATENT DOCUMENTS

| | | |
|---|---|---|
| EP | 1 033 405 | 9/2000 |
| WO | WO 99/58654 | 11/1999 |
| WO | WO01/83697 | 11/2001 |
| WO | WO 03/079766 | 10/2003 |

OTHER PUBLICATIONS

Blast.pdf Mar. 13, 2010.*
Cobolt.pdf Mar. 13, 2010.*
Anoop et al., "Modulation of citrate metabolism alters aluminum tolerance in yeast and transgenic canola overexpressing a mitochondrial citrate synthase," *Plant Physiol.*, 132:2205-2217, 2003.
Beisson et al., "Arabidopsis genes involved in acyl lipid metabolism. A 2003 census of the candidates, a study of the distribution of expressed sequence tags in organs, and a web-based database," *Plant Physiol.*, 132:681-697, 2003.
Bert et al., "Comparative genetic analysis of quantitative traits in sunflower (*Helianthus annuus* L.). 2. Characterisation of QTL involved in developmental and agronomic traits," *Theor. Appl. Genet.*, 107:181-189, 2003.
Colbert et al., "High-throughput screening for induced point mutations," *Plant Physiol.*, 126(2):480-484, 2001.
Dehesh et al., "Overexpression of 3-ketoacyl-acyl-carrier protein synthase IIIs in plants reduces the rate of lipid synthesis," *Plant Physiol.*, 125:1103-1114, 2001.
Eastmond and Graham, "Re-examining the role of glyoxylate cycle in oilseeds," *Trends Plant Sci.*, 6(2):72-77, 2001.
Eccleston and Ohlrogge, "Expressions of lauroyl-acyl carrier protein thioesterase in *Brassica napus* seeds induces pathways for both fatty acid oxidation and biosynthesis and implies a set point for triacylglycerol accumulation," *Plant Cell.* 10:613-621, 1998.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in Arabidopsis," *Plant Cell*, 17:182-203, 2005.
Feldmann et al., "A Dwarf Mutant of Arabidopsis Generated by T-DNA Insertion Mutagenesis," *Science*, 243(4896):1351-1354, 1989.
Focks and Benning, "*wrinkled1*: A novel, low-seed-oil mutant of Arabidopsis with a deficiency in the seed-specific regulation of carbohydrate metabolism," *Plant Physiol.*, 118:91-101, 1998.
Girke et al., "Microarray analysis of developing Arabidopsis seeds," *Plant Physiol.*, 124:1570-1581, 2000.
Jako et al., "Seed-specific over-expression of an Arabidopsis cDNA encoding a diacylglycerol acyltransferase enhances seed oil content and seed weight," *Plant Physiol.*, 126(2):861-874, 2001.
James and Dooner, "Isolation of EMS-induced mutants in Arabidopsis altered in seed fatty acid composition," *Theor. Appl. Genet.*, 80(2):241-245, 1990.
Kang and Singh, "Characterization of salicylic acid-responsive, arabidopsis Dof domain proteins: overexpression of OBP3 leads to growth defects," *The Plant Journal*, 21(4):329-339, 2000.
Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409, 1995.
Katavic et al., "Utility of the *Arabidopsis FAE1* and yeast *SLC1-1* genes for improvements in erucic acid and oil content in rapeseed," *Biochem Soc. Trans.*, 28(6):935-937, 2000.
Larson et al., "Acyl CoA profiles of transgenic plants that accumulate medium-chain fatty acids indicate inefficient storage lipid synthesis in developing oilseeds," *Plant J.*, 32:519-527, 2002.

(Continued)

*Primary Examiner*—Eileen B O Hara
(74) *Attorney, Agent, or Firm*—Donald R. Stuart; Klarquist Sparkman LLP

(57) ABSTRACT

The present invention is directed to isolated HIO41 nucleic acid and protein, and to plants that display an altered oil content phenotype due to altered expression of a HIO41 nucleic acid. The invention is further directed to methods of generating plants with an altered oil content phenotype.

6 Claims, No Drawings

OTHER PUBLICATIONS

Lemieux et al., "Mutants of Arabidopsis with alterations in seed lipid fatty acid composition," *Theor. Appl. Genet.*, 80(2):234-240, 1990.

Lin et al., "The Pex16p homolog SSE1 and storage organelle formation in *Arabidopsis* seeds," *Science*. 284:328-330, 1999.

Lionneton et al., "Development of an AFLP-based linkage map and localization of QTLs for seed fatty acid content in condiment mustard (*Brassica juncea*)," *Genome*, 45(6):1203-1215, 2002.

Liu and Butow, "A transcriptional switch in the expression of yeast tricarboxylic acid cycle genes in response to a reduction or loss of respiratory function," *Mol. Cell. Biol.*, 19:6720-6728, 1999.

McCallum et al., "Targeted screening for induced mutations," *Nat. Biotechnol.*, 18(4):455-457, 2000.

Mekhedov et al., "Toward a functional catalog of the plant genome. A survey of genes for lipid biosynthesis," *Plant Physiol.*, 122:389-401, 2000.

Moire et al., "Impact of unusual fatty acid synthesis on futile cycling through β-oxidation and on gene expression in transgenic plants," *Plant Physiol.*, 134:432-442, 2004.

Neuhaus and Emes, "Nonphotosynthetic Metabolism In Plastids," *Annu. Rev. Plant Physiol. Plant Mol. Biol.*, 51:111-140, 2000.

O'Hara et al., "Fatty acid and lipid biosynthetic genes are expressed at constant molar ratios but different absolute levels during embryogenesis," *Plant Physiol.*, 129:310-320, 2002.

Okuley et al., "Arabidopsis FAD2 Gene Encodes the Enzyme That Is Essential for Polyunsaturated Lipid Synthesis," *Plant Cell*, 6:147-158, 1994.

Plesch et al., "Involvement of TAAAG elements suggests a role for Dof transcription factors in guard cell-specific gene expression," *The Plant Journal*, 28(4):455-464, 2001.

Pritchard et al., "Germination and storage reserve mobilization are regulated independently in *Arabidopsis*," *Plant J.*, 31(5):639-647, 2002.

Rangasamy and Ratledge, "Compartmentation of ATP:Citrate lyase in plants," *Plant Physiol.*, 122:1225-1230, 2000.

Rangasamy and Ratledge, "Genetic enhancement of fatty acid synthesis by targeting rat liver ATP:citrate lyase into plastids of tobacco," *Plant Physiol.*, 122:1231-1238, 2000.

Ratledge et al, "Correlation of ATP/citrate lyase activity with lipid accumulation in developing seeds of *Brassica napus* L.," *Lipids*, 32(1):7-12, 1997.

Rawsthorne, S., "Carbon flux and fatty acid synthesis in plants," *Prog Lipid Res.*, 41:182-196, 2002.

Ruuska et al., "Contrapuntal networks of gene expression during Arabidopsis seed filling," *Plant Cell*, 14:1191-1206, 2002.

Rylott et al., "Co-ordinate regulation of genes involved in storage lipid mobilization in *Arabidopsis thaliana*," *Biochem Soc. Trans.*, 29:283-287, 2001.

Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.

Schnurr et al., "Characterization of an acyl-CoA synthetase from *Arabidopsis thaliana*," *Biochem Soc. Trans.*, 28(6):957-958, 2000.

Shockey et al., "Characterization of the AMP-binding protein gene family in *Arabidopsis thaliana*: will the real acyl-CoA synthetases please stand up?" *Biochem Soc. Trans.*, 28(6):955-957, 2000.

Thelen et al., "Biotin carboxyl carrier protein isoforms in Brassicaceae oilseeds," *Biochem. Soc. Trans.*, 28(6):595-598, 2000.

Wada et al., "Role of a positive regulator of root hair development, CAPRICE, in Arabidopsis root epidermal cell differentiation," *Development*, 129(23):5409-5419, 2002.

White et al., "A new set of Arabidopsis expressed sequence tags from developing seeds. The metabolic pathway from carbohydrates to seed oil," *Plant Physiol.*, 124:1582-1594, 2000.

Yadav et al., "Cloning of higher plant omega-3 fatty acid desaturases," *Plant Physiol.*, 103(2):467-476, 1993.

Yanagisawa and Sheen, "Involvement of maize Dof zinc finger proteins in tissue-specific and light-regulated gene expression," *Plant Cell*, 10:75-89, 1998.

Yanagisawa and Schmidt, "Diversity and similarity among recognition sequences of Dof transcription factors," *The Plant Journal*, 17(2):209-214, 1999.

Yanagisawa, S., "The Dof family of plant transcription factors," *Trends in Plant Science*, 7(12):555-560, 2002.

\* cited by examiner

GENERATION OF PLANTS WITH ALTERED OIL CONTENT

REFERENCE TO RELATED APPLICATIONS

This application is the U.S. National Stage of International Application No. PCT/US2005/013398, filed Apr. 20, 2005, which was published in English under PCT Article 21(2), which in turn claims the benefit of U.S. Provisional Application Ser. No. 60/564,532, filed Apr. 22, 2004, the contents of which are hereby incorporated by reference.

BACKGROUND OF THE INVENTION

The ability to manipulate the composition of crop seeds, particularly the content and composition of seed oils, has important applications in the agricultural industries, relating both to processed food oils and to oils for animal feeding. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remainder is sold principally for lower value livestock feed (U.S. Soybean Board, 2001 Soy Stats). Canola seed is crushed to produce oil and the co-product canola meal (Canola Council of Canada). Nearly 20% of the 1999/2000 U.S. corn crop was industrially refined, primarily for production of starch, ethanol and oil (Corn Refiners Association). Thus, it is often desirable to maximize oil content of seeds. For instance, for processed oilseeds such as soy and canola, increasing the absolute oil content of the seed will increase the value of such grains. For processed corn it may be desired to either increase or decrease oil content, depending on utilization of other major constituents. Decreasing oil may improve the quality of isolated starch by reducing undesired flavors associated with oil oxidation. Alternatively, in ethanol production, where flavor is unimportant, increasing oil content may increase overall value. In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors.

Biotechnological manipulation of oils can provide compositional alteration and improvement of oil yield. Compositional alterations include high oleic soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil contents in current HOC fields have plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

The most obvious target crops for the processed oil market are soy, corn and rapeseed, and a large body of commercial work (e.g., U.S. Pat. No. 5,952,544; PCT application WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990; James and Dooner, 1990). T-DNA mutagenesis screens (Feldmann et al., 1989) that detected altered fatty acid composition identified the omega 3 desaturase (FAD3) and delta-12 desaturase (FAD2) genes (U.S. Pat. No. 5,952,544; Yadav et al., 1993; Okuley et al., 1994). A screen which focused on oil content rather than oil quality, analyzed chemically-induced mutants for wrinkled seeds or altered seed density, from which altered seed oil content was inferred (Focks and Benning, 1998). Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al, 1995). It was further shown that seed-specific over-expression of the DGAT cDNA was associated with increased seed oil content (Jako et al., 2001).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (Hayashi et al., 1992; Weigel D et al. 2000). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, Schaffer et al., 1998, Fridborg et al., 1999; Kardailsky et al., 1999; Christensen S et al. 1998).

SUMMARY OF THE INVENTION

The invention provides a transgenic plant having a high oil phenotype. The transgenic plant comprises a transformation vector comprising a nucleotide sequence that encodes or is complementary to a sequence that encodes a High Oil (hereinafter "HIO41") polypeptide. In preferred embodiments, the transgenic plant is selected from the group consisting of rapeseed, soy, corn, sunflower, cotton, cocoa, safflower, oil palm, coconut palm, flax, castor and peanut. The invention further provides a method of producing oil comprising growing the transgenic plant and recovering oil from said plant.

The transgenic plant of the invention is produced by a method that comprises introducing into progenitor cells of the plant a plant transformation vector comprising a nucleotide sequence that encodes or is complementary to a sequence that encodes a HIO41 polypeptide, and growing the transformed progenitor cells to produce a transgenic plant, wherein the HIO41 polynucleotide sequence is expressed causing the high oil phenotype.

The present invention also provides a container of over about 10,000, more preferably about 20,000, and even more preferably about 40,000 seeds where over about 10%, more preferably about 25%, more preferably about 50%, and even more preferably about 75% or more preferably about 90% of the seeds are seeds derived from a plant of the present invention.

The present invention also provides a container of over about 10 kg, more preferably about 25 kg, and even more preferably about 50 kg seeds where over about 10%, more preferably about 25%, more preferably about 50%, and even more preferably about 75% or more preferably about 90% of the seeds are seeds derived from a plant of the present invention.

Any of the plants or parts thereof of the present invention may be processed to produce a feed, meal, or oil preparation. A particularly preferred plant part for this purpose is a seed. In a preferred embodiment the feed, meal, or oil preparation is designed for ruminant animals. Methods to produce feed, meal, and oil preparations are known in the art. See, for example, U.S. Pat. Nos. 4,957,748; 5,100,679; 5,219,596; 5,936,069; 6,005,076; 6,146,669; and 6,156,227. The meal of the present invention may be blended with other meals. In a preferred embodiment, the meal produced from plants of the present invention or generated by a method of the present invention constitutes greater than about 0.5%, about 1%, about 5%, about 10%, about 25%, about 50%, about 75%, or about 90% by volume or weight of the meal component of any product. In another embodiment, the meal preparation may be blended and can constitute greater than about 10%, about 25%, about 35%, about 50%, or about 75% of the blend by volume.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, propagules, and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (i.e., a genotypically similar plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality. An "altered oil content phenotype" refers to measurable phenotype of a genetically modified plant, where the plant displays a statistically significant increase or decrease in overall oil content (i.e., the percentage of seed mass that is oil), as compared to the similar, but non-modified plant. A high oil phenotype refers to an increase in overall oil content.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a Ti plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic. Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) Agrobacterium-mediated transformation methods.

The most commonly used methods for transformation of plant cells are the Agrobacterium-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

Agrobacterium-mediated transformation is achieved through the use of a genetically engineered soil bacterium belonging to the genus Agrobacterium. A number of wild-type and disarmed strains of Agrobacterium tumefaciens and Agrobacterium rhizogenes harboring Ti or Ri plasmids can be used for gene transfer into plants. Gene transfer is done via the transfer of a specific DNA known as "T-DNA" that can be genetically engineered to carry any desired piece of DNA into many plant species.

Agrobacterium-mediated genetic transformation of plants involves several steps. The first step, in which the virulent Agrobacterium and plant cells are first brought into contact with each other, is generally called "inoculation". Following the inoculation, the Agrobacterium and plant cells/tissues are permitted to be grown together for a period of several hours to several days or more under conditions suitable for growth and T-DNA transfer. This step is termed "co-culture". Following co-culture and T-DNA delivery, the plant cells are treated with bactericidal or bacteriostatic agents to kill the Agrobacterium remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318 (Adams et al.); U.S. Pat. No. 5,538,880 (Lundquist et. al.), U.S. Pat. No. 5,610,042 (Chang et al.); and PCT Publication WO 95/06128 (Adams et al.); each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (International Publication No. WO 95/06128 (Adams et al.)), barley, wheat (U.S. Pat. No. 5,563,055 (Townsend et al.) incorporated herein by reference in its entirety), rice, oat, rye, sugarcane, and sorghum; as well as a number of dicots including tobacco, soybean (U.S. Pat. No. 5,322,783 (Tomes et al.), incorporated herein by reference in its entirety), sunflower, peanut, cotton, tomato, and legumes in general (U.S. Pat. No. 5,563,055 (Townsend et al.) incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061 (Barry, et al.), U.S. Pat. No. 5,633,435 (Barry, et al.), and U.S. Pat. No. 6,040,497 (Spencer, et al.) and aroA described in U.S. Pat. No. 5,094,945 (Comai) for glyphosate tolerance; a polynucleotide molecule encoding bromoxynil nitrilase (Bxn) described in U.S. Pat. No. 4,810,648 (Duerrschnabel, et al.) for Bromoxynil tolerance; a polynucleotide molecule encoding phytoene desaturase (crtI) described in Misawa et al, (1993) Plant J. 4:833-840 and Misawa et al, (1994) Plant J. 6:481-489 for norflurazon tolerance; a polynucleotide molecule encoding acetohydroxyacid synthase (AHAS, aka ALS) described in Sathasiivan et al. (1990) Nucl. Acids Res. 18:2188-2193 for tolerance to sulfonylurea herbicides; and the bar gene described in DeBlock, et al. (1987) EMBO J. 6:2513-2519 for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Altered Oil Content Phenotype

An *Arabidopsis* activation tagging screen was used to identify the association between the gene we have designated "HIO41," (At5g60200, GI#42568667) encoding a Dof-type zinc finger domain-containing protein (GI#18424330), and an altered oil content phenotype (specifically, a high oil phenotype). Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al, 2000). When the T-DNA inserts into the genome of transformed plants, the enhancer element can cause up-regulation genes in the vicinity, generally within about 10 kilobase (kb) of the insertion. T1 plants were exposed to the selective agent in order to specifically recover transformed plants that expressed the selectable marker and therefore harbored T-DNA insertions. Samples of approximately 15-20 T2 seeds were collected from transformed T1 plants, and lipids were extracted from whole seeds. Gas chromatography (GC)/FID analysis was performed to determine fatty acid content and composition of seed samples.

An *Arabidopsis* line that showed a high-oil phenotype was identified. The association of the HIO41 gene with the high oil phenotype was discovered by analysis of the genomic DNA sequence flanking the T-DNA insertion in the identified line. Accordingly, HIO41 genes and/or polypeptides may be employed in the development of genetically modified plants having a modified oil content phenotype ("a HIO41 phenotype"). HIO41 genes may be used in the generation of oilseed crops that provide improved oil yield from oilseed processing and in the generation of feed grain crops that provide increased energy for animal feeding. HIO41 genes may further be used to increase the oil content of specialty oil crops, in order to augment yield of desired unusual fatty acids. Transgenic plants that have been genetically modified to express HIO41 can be used in the production of oil, wherein the transgenic plants are grown, and oil is obtained from plant parts (e.g., seed) using standard methods.

HIO41 Nucleic Acids and Polypeptides

The invention provides novel *Arabidopsis* HIO41 nucleic acid, as presented in SEQ ID NO:1 and in Genbank entry GI#42568667. The invention further provides HIO41 protein sequence, as presented in SEQ ID NO:2 and in GI#18424330. Nucleic acids and/or proteins that are orthologs or paralogs of *Arabidopsis* HIO41 are described in Example 4 below.

As used herein, the term "HIO41 polypeptide" refers to a full-length HIO41 protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active HIO41 polypeptide causes an altered oil content phenotype when mis-expressed in a plant. In a further preferred embodiment, mis-expression of the HIO41 polypeptide causes a high oil phenotype in a plant. In another embodiment, a functionally active HIO41 polypeptide is capable of rescuing defective (including deficient) endogenous HIO41 activity when expressed in a plant or in plant cells; the rescuing polypeptide may be from the same or from a different species as that with defective activity. In another embodiment, a functionally active fragment of a full length HIO41 polypeptide (i.e., a native polypeptide having the sequence of SEQ ID NO:2 or a naturally occurring ortholog thereof) retains one of more of the biological properties associated with the full-length HIO41 polypeptide, such as signaling activity, binding activity, catalytic activity, or cellular or extra-cellular localizing activity.

Functionally active variants of full-length HIO41 polypeptides or fragments thereof include polypeptides with amino acid insertions, deletions, or substitutions that retain one of more of the biological properties associated with the full-length HIO41 polypeptide. In some cases, variants are generated that change the post-translational processing of a HIO41 polypeptide. For instance, variants may have altered protein transport or protein localization characteristics or altered protein half-life compared to the native polypeptide.

As used herein, the term "HIO41 nucleic acid" encompasses nucleic acids with the sequence provided in or complementary to the sequence provided in SEQ ID NO:1, as well as functionally active fragments, derivatives, or orthologs thereof. A HIO41 nucleic acid of this invention may be DNA, derived from genomic DNA or cDNA, or RNA.

In one embodiment, a functionally active HIO41 nucleic acid encodes or is complementary to a nucleic acid that encodes a functionally active HIO41 polypeptide. Included within this definition is genomic DNA that serves as a template for a primary RNA transcript (i.e., an mRNA precursor) that requires processing, such as splicing, before encoding the functionally active HIO41 polypeptide. A HIO41 nucleic acid can include other non-coding sequences, which may or may not be transcribed; such sequences include 5' and 3'UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO41 polypeptide, or an intermediate form. A HIO41 polynucleotide can also include heterologous coding sequences, for example, sequences that encode a marker included to facilitate the purification of the fused polypeptide, or a transformation marker.

In another embodiment, a functionally active HIO41 nucleic acid is capable of being used in the generation of loss-of-function HIO41 phenotypes, for instance, via antisense suppression, co-suppression, etc.

In one preferred embodiment, a HIO41 nucleic acid used in the methods of this invention comprises a nucleic acid sequence that encodes or is complementary to a sequence that encodes a HIO41 polypeptide having at least 50%, 60%, 70%, 75%, 80%, 85%, 90%, 95% or more sequence identity to the polypeptide sequence presented in SEQ ID NO:2.

In another embodiment a HIO41 polypeptide of the invention comprises a polypeptide sequence with at least 50% or 60% identity to the HIO41 polypeptide sequence of SEQ ID NO:2, and may have at least 70%, 80%, 85%, 90% or 95% or more sequence identity to the HIO41 polypeptide sequence of SEQ ID NO:2. In another embodiment, a HIO41 polypeptide comprises a polypeptide sequence with at least 50%, 60%, 70%, 80%, 85%, 90% or 95% or more sequence identity to a functionally active fragment of the polypeptide presented in SEQ ID NO:2, such as a Dof-type zinc finger domain. In yet another embodiment, a HIO41 polypeptide comprises a polypeptide sequence with at least 50%, 60%, 70%, 80%, or 90% identity to the polypeptide sequence of SEQ ID NO:2 over its entire length and comprises a Dof-type zinc finger domain.

In another aspect, a HIO41 polynucleotide sequence is at least 50% to 60% identical over its entire length to the HIO41 nucleic acid sequence presented as SEQ ID NO:1, or nucleic acid sequences that are complementary to such a HIO41 sequence, and may comprise at least 70%, 80%, 85%, 90% or 95% or more sequence identity to the HIO41 sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1990) 215:403-410) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that hybridize to the nucleic acid sequence of SEQ ID NO:1. The stringency of hybridization can be controlled by temperature, ionic strength, pH, and the presence of denaturing agents such as formamide during hybridization and washing. Conditions routinely used are well known (Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of SEQ ID NO:1 under stringent hybridization conditions that are: prehybridization of filters containing nucleic acid for 8 hours to overnight at 65° C. in a solution comprising 6× single strength citrate (SSC)(1× SSC is 0.15 M NaCl, 0.015 M Na citrate; pH 7.0), 5× Denhardt's solution, 0.05% sodium pyrophosphate and 100 µg/ml herring sperm DNA; hybridization for 18-20 hours at 65° C. in a solution containing 6× SSC, 1× Denhardt's solution, 100 µg/ml yeast tRNA and 0.05% sodium pyrophosphate; and washing of filters at 65° C. for 1 h in a solution containing 0.1× SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5× SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5× SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2× SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO41 polypeptide can be produced. For example, codons may be selected to increase the rate at which expression of the polypeptide occurs in a particular host species, in accordance with the optimum codon usage dictated by the particular host organism (Nakamura et al, 1999). Such sequence variants may be used in the methods of this invention.

The methods of the invention may use orthologs of the *Arabidopsis* HIO41. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210).

Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (Sambrook, 1989; Dieffenbach and Dveksler, 1995). For instance, methods for generating a cDNA library from the plant species of interest and probing the library with partially homologous gene probes are described in Sambrook et al. A highly conserved portion of the *Arabidopsis* HIO41 coding sequence may be used as a probe. HIO41 ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known HIO41 polypeptides are used for ortholog isolation (Harlow and Lane, 1988, 1999). Western blot analysis can determine that a HIO41 ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which HIO41 nucleic acid and/or polypeptide sequences have been identified.

HIO41 nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991), may be used to introduce desired changes into a cloned nucleic acid.

In general, the methods of the invention involve incorporating the desired form of the HIO41 nucleic acid into a plant expression vector for transformation of in plant cells, and the HIO41 polypeptide is expressed in the host plant.

An isolated HIO41 nucleic acid molecule is other than in the form or setting in which it is found in nature and is identified and separated from least one contaminant nucleic acid molecule with which it is ordinarily associated in the natural source of the HIO41 nucleic acid. However, an isolated HIO41 nucleic acid molecule includes HIO41 nucleic acid molecules contained in cells that ordinarily express HIO41 where, for example, the nucleic acid molecule is in a chromosomal location different from that of natural cells.

Generation of Genetically Modified Plants with an Altered Oil Content Phenotype

HIO41 nucleic acids and polypeptides may be used in the generation of genetically modified plants having a modified oil content phenotype. As used herein, a "modified oil content phenotype" may refer to modified oil content in any part of the plant; the modified oil content is often observed in seeds. In a preferred embodiment, altered expression of the HIO41 gene in a plant is used to generate plants with a high oil phenotype.

The methods described herein are generally applicable to all plants. Although activation tagging and gene identification is carried out in *Arabidopsis*, the HIO41 gene (or an ortholog, variant or fragment thereof) may be expressed in any type of plant. In a preferred embodiment, the invention is directed to oil-producing plants, which produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Li-*

*num usitatissimum*), castor (*Ricinus communis*) and peanut (*Arachis hypogaea*). The invention may also be directed to fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species that may be a source of unique fatty acids.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO41 polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as rapeseed (De Block et al., 1989), sunflower (Everett et al., 1987), and soybean (Christou et al., 1989; Kline et al., 1987).

Expression (including transcription and translation) of HIO41 may be regulated with respect to the level of expression, the tissue type(s) where expression takes place and/or developmental stage of expression. A number of heterologous regulatory sequences (e.g., promoters and enhancers) are available for controlling the expression of a HIO41 nucleic acid. These include constitutive, inducible and regulatable promoters, as well as promoters and enhancers that control expression in a tissue- or temporal-specific manner. Exemplary constitutive promoters include, but are not limited to, the raspberry E4 promoter (U.S. Pat. Nos. 5,783,393 and 5,783,394), the nopaline synthase (NOS) promoter (Ebert et al., *Proc. Natl. Acad. Sci.* (*U.S.A.*) 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al, 1992), the melon actin promoter (published PCT application WO0056863), the figwort mosaic virus 35S-promoter (U.S. Pat. No. 5,378,619), the light-inducible promoter from the small subunit of ribulose-1,5 -bis-phosphate carboxylase (ssRUBISCO), the Adh promoter (Walker et al., *Proc. Natl. Acad. Sci.* (*U.S.A*) 84:6624-6628, 1987), the sucrose synthase promoter (Yang et al., *Proc. Natl. Acad. Sci.* (*U.S.A*) 87:4144-4148, 1990), the R gene complex promoter (Chandler et al., *The Plant Cell* 1:1175-1183, 1989), the chlorophyll a/b binding protein gene promoter the CsVMV promoter (Verdaguer B et al., 1998), these promoters have been used to create DNA constructs that have been expressed in plants; e.g., PCT publication WO 84/02913. Exemplary tissue-specific promoters include the tomato E4 and E8 promoters (U.S. Pat. No. 5,859,330) and the tomato 2AII gene promoter (Van Haaren M J J et al., 1993).

In one preferred embodiment, HIO41 expression is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219, 1991), globulin (Belanger and Kriz, *Genet.*, 129: 863-872, 1991, GenBank Accession No. L22295), gamma zein Z 27 (Lopes et al., *Mol Gen Genet.*, 247:603-613, 1995), L3 oleosin promoter (U.S. Pat. No. 6,433,252), phaseolin (Bustos et al., *Plant Cell*, 1(9):839-853, 1989), arcelin5 (US 2003/0046727), a soybean 7S promoter, a 7Sα promoter (US 2003/0093828), the soybean 7Sα' beta conglycinin promoter, a 7S α' promoter (Beachy et al., *EMBO J.*, 4:3047, 1985; Schuler et al., *Nucleic Acid Res.*, 10(24):8225-8244, 1982), soybean trypsin inhibitor (Riggs et al., *Plant Cell* 1(6):609-621, 1989), ACP (Baerson et al., *Plant Mol. Biol.*, 22(2):255-267, 1993), stearoyl-ACP desaturase (Slocombe et al., *Plant Physiol.* 104(4):167-176, 1994), soybean a' subunit of β-conglycinin (Chen et al., *Proc. Natl. Acad. Sci.* 83:8560-8564, 1986), *Vicia faba* USP (P-Vf.Usp, SEQ ID NO: 1, 2, and 3 in (US 2003/229918) and *Zea mays* L3 oleosin promoter (Hong et al., *Plant Mol. Biol.*, 34(3):549-555, 1997). Also included are the zeins, which are a group of storage proteins found in corn endosperm. Genomic clones for zein genes have been isolated (Pedersen et al., *Cell* 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba legumin* (Baumlein et al., 1991, Mol Gen Genet 225: 121-8; Baumlein et al., 1992, *Plant J* 2:233-9), *V. faba usp* (Fiedler et al., 1993, Plant Mol Biol 22:669-79), pea *convicilin* (Bown et al., 1988, Biochem J 251:717-26), pea *lectin* (dePater et al., 1993, Plant Cell 5:877-86), *P. vulgaris beta phaseolin* (Bustos et al., 1991, EMBO J 10: 1469-79), *P. vulgaris* DLEC2 and PHS [beta] (Bobb et al, 1997, Nucleic Acids Res 25:641-7), and soybean *beta-Conglycinin*, 7S storage protein (Chamberland et al., 1992, Plant Mol Biol 19:937-49).

Cereal genes whose promoters are associated with early seed and embryo development include rice *glutelin* ("GluA-3," Yoshihara and Takaiwa, 1996, Plant Cell Physiol 37:107-11; "GluB-1," Takaiwa et al., 1996, Plant Mol Biol 30:1207-21; Washida et al., 1999, Plant Mol Biol 40:1-12; "Gt3," Leisy et al., 1990, Plant Mol Biol 14:41-50), rice *prolamin* (Zhou &

Fan, 1993, Transgenic Res 2:141-6), wheat *prolamin* (Hammond-Kosack et al., 1993, EMBO J 12:545-54), maize *zein* (Z4, Matzke et al., 1990, Plant Mol Biol 14:323-32), and barley *B-hordeins* (Entwistle et al., 1991, Plant Mol Biol 17:1217-31).

Other genes whose promoters are associated with early seed and embryo development include oil palm GLO7A (7S globulin, Morcillo et al., 2001, Physiol Plant 112:233-243), *Brassica napus napin*, 2S storage protein, and napA gene (Josefsson et al., 1987, J Biol Chem 262:12196-201; Stalberg et al., 1993, Plant Mol Biol 1993 23:671-83; Ellerstrom et al., 1996, Plant Mol Biol 32:1019-27), *Brassica napus oleosini* (Keddie et al., 1994, Plant Mol Biol 24:327-40), *Arabidopsis oleosini* (Plant et al., 1994, Plant Mol Biol 25:193-205), *Arabidopsis* FAE1 (Rossak et al., 2001, Plant Mol Biol 46:717-25), *Canavalia gladiata* conA (Yamamoto et al., 1995, Plant Mol Biol 27:729-41), and *Catharanthus roseus* strictosidine synthase (Str, Ouwerkerk and Memelink, 1999, Mol Gen Genet 261:635-43). In another preferred embodiment, regulatory sequences from genes expressed during oil biosynthesis are used (U.S. Pat. No. 5,952,544). Alternative promoters are from plant storage protein genes (Bevan et al, 1993, Philos Trans R Soc Lond B Biol Sci 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In yet another aspect, in some cases it may be desirable to inhibit the expression of endogenous HIO41 in a host cell. Exemplary methods for practicing this aspect of the invention include, but are not limited to antisense suppression (Smith, et al., 1988; van der Krol et al., 1988); co-suppression (Napoli, et al., 1990); ribozymes (PCT Publication WO 97/10328); and combinations of sense and antisense (Waterhouse, et al., 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988), a partial cDNA sequence including fragments of 5' coding sequence, (Cannon et al., 1990), or 3' non-coding sequences (Ch'ng et al., 1989). Cosuppression techniques may use the entire cDNA sequence (Napoli et al., 1990; van der Krol et al., 1990), or a partial cDNA sequence (Smith et al., (1990).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, Baulcombe D, 1999]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Oil Content Phenotype

The invention further provides a method of identifying plants that have mutations in endogenous HIO41 that confer altered oil content, and generating altered oil content progeny of these plants that are not genetically modified. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. HIO41-specific PCR is used to identify whether a mutated plant has a HIO41 mutation. Plants having HIO41 mutations may then be tested for altered oil content, or alternatively, plants may be tested for altered oil content, and then HIO41-specific PCR is used to determine whether a plant having altered oil content has a mutated HIO41 gene. TILLING can identify mutations that may alter the expression of specific genes or the activity of proteins encoded by these genes (Colbert et al (2001) Plant Physiol 126:480-484; McCallum et al (2000) Nature Biotechnology 18:455-457).

In another method, a candidate gene/Quantitative Trait Locus (QTLs) approach can be used in a marker-assisted breeding program to identify alleles of or mutations in the HIO41 gene or orthologs of HIO41 that may confer altered oil content (Bert et al., Theor Appl Genet. 2003 June;107(1):181-9; and Lionneton et al, Genome. 2002 December;45(6):1203-15). Thus, in a further aspect of the invention, a HIO41 nucleic acid is used to identify whether a plant having altered oil content has a mutation in endogenous HIO41 or has a particular allele that causes altered oil content.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced public databases are also incorporated by reference.

EXAMPLES

Example 1

Generation of Plants with a HIO41 Phenotype by Transformation with an Activation Tagging Construct Mutants were generated using the activation tagging "ACTTAG" vector, pSKI015 (GI 6537289; Weigel D et al., 2000). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4× CaMV 35S enhancer element. Transgenic plants were selected at the T1 generation based on herbicide resistance. T2 seed was collected from T1 plants and stored in an indexed collection, and a portion of the T2 seed was accessed for the screen.

Quantitative determination of seed fatty acid content was performed using the follows methods. An aliquot of 15 to 20 T2 seeds from each line tested, which generally contained homozygous insertion, homozygous wild-type, and heterozygous genotypes in a standard 1:1:2 ratio, was massed on UMT-2 ultra-microbalance (Mettler-Toledo Co., Ohio, USA) and then transferred to a glass extraction vial. Whole seeds were trans-esterified in 500 ul 2.5% $H_2SO_4$ in MeOH for 3 hours at 80° C., following the method of Browse et al. (Biochem J 235:25-31, 1986) with modifications. A known amount of heptadecanoic acid was included in the reaction as an internal standard. 750 ul of water and 400 ul of hexane were added to each vial, which was then shaken vigorously and allowed to phase separate. Reaction vials were loaded directly onto GC for analysis and the upper hexane phase was sampled by the autosampler. Gas chromatography with Flame Ionization detection was used to separate and quantify the fatty acid methyl esters. Agilent 6890 Plus GC's were used for separation with Agilent Innowax columns (30 m×0.25 mm ID, 250 um film thickness). The carrier gas was Hydrogen at a constant flow of 2.5 ml/minute. 1 ul of sample was injected in splitless mode (inlet temperature 220° C., Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis was using the Millennium Chromatography Management System (Version 3.2, Waters Corporation, Milford, Mass.). Integration and quantification were performed automatically, but all analyses were subsequently examined manually to verify correct peak identification and acceptable signal to noise ratio before inclusion of the derived results in the study. The ACTTAG line designated HIO41 was identified as having a high oil phenotype. Fatty acids constituted 31.6 oil (w/w) of seed mass, compared to an average of 26.5% (w/w) oil in control plants.

Example 2

Characterization of the T-DNA Insertion in Plants Exhibiting the Altered Oil Content Phenotype.

We performed standard molecular analyses, essentially as described in patent application PCT WO0183697, to determine the site of the T-DNA insertion associated with the altered oil content phenotype. Briefly, genomic DNA was extracted from plants exhibiting the altered oil content phenotype. PCR, using primers specific to the pSKI015 vector, confirmed the presence of the 35S enhancer in plants from the HIO41 line, and Southern blot analysis verified the genomic integration of the ACTTAG T-DNA. The HIO41 mutant line has one T-DNA locus which co-segregated with the high oil phenotype. T2 individuals homozygous for the High Oil locus produced seeds which had a mean oil content of 101.5% (n=4) of the reference. Hemizygous lines produced seeds which had a mean oil content of 99.2% of the reference (n=8) and Null segregant produced seeds which had a mean oil content of 95.3% of the reference (n=6). Candidate genes located within 10 kb of the T-DNA insert were identified and evaluated. One of those genes, At5g60200, when overexpressed in transgenic plants, recapitulated the high oil phenotype as described in Example 3 below. Inverse PCR was used to recover genomic DNA adjacent to the left border of the T-DNA.

T2 seeds from plants over-expressing At5g60200 have higher seed oil content (34.36% oil) than their wild-type controls (32.38% oil) using Calibration 2. The difference in seed oil content between plants over-expressing At5g60200 and the wild-type is significant [t-test analysis (t-test, 2-tailed, 2-sample unequal variance: P=0.024 for Calibration 2)].

Example 3

Recapitulation of HIO41 Phenotype

To test whether over-expression of At5g60200 causes a high seed oil phenotype, oil content in seeds from transgenic plants over-expressing this gene was compared with oil content in seeds from non-transgenic control plants. To do this, At5g60200 was cloned into a plant transformation vector behind the seed specific CsVMV promoter and transformed into *Arabidopsis* plants using the floral dip method. The plant transformation vector contains the nptII gene, which provides resistance to kanamyacin, and serves as a selectable marker. Seed from the transformed plants were plated on agar medium containing kanamycin. After 7 days, transgenic plants were identified as healthy green plants and transplanted to soil. Non-transgenic control plants were germinated on agar medium, allowed to grow for 7 days and then transplanted to soil. Twenty-two transgenic seedlings and 10 non-transgenic control plants were transplanted to random positions in the same 32 cell flat. The plants were grown to maturity, allowed to self-fertilize and set seed. Seed was harvested from each plant and its oil content estimated by Near Infrared (NIR) Spectroscopy using methods previously described.

The effect of over-expression of At5g60200 on seed oil has been tested in two experiments. In both experiments, the plants over-expressing At5g60200 had higher seed oil content than the control plants grown in the same flat. Across the experiments, the average seed oil content of plants over-expressing At5g60200 was 6.0% greater than the untransformed controls. The in seed oil content in plants over-expressing At5g60200 was significantly greater than non-transgenic control plants (two-way ANOVA; P=0.0013).

| Experiment | Plant ID | Transgene | Predicted average | Relative value average |
|---|---|---|---|---|
| 1 | DX02713001 | CsVMV::At5g60200 | 35.2238 | 108.7993 |
| 1 | DX02713002 | CsVMV::At5g60200 | 36.5548 | 112.9104 |
| 1 | DX02713003 | CsVMV::At5g60200 | 32.8341 | 101.4181 |

-continued

| Experiment | Plant ID | Transgene | Predicted average | Relative value average |
|---|---|---|---|---|
| 1 | DX02713004 | CsVMV::At5g60200 | 36.7385 | 113.4781 |
| 1 | DX02713005 | CsVMV::At5g60200 | 36.0392 | 111.3179 |
| 1 | DX02713006 | CsVMV::At5g60200 | 34.0595 | 105.2031 |
| 1 | DX02713007 | CsVMV::At5g60200 | 35.7697 | 110.4855 |
| 1 | DX02713008 | CsVMV::At5g60200 | 34.1471 | 105.4737 |
| 1 | DX02713009 | CsVMV::At5g60200 | 34.6806 | 107.1217 |
| 1 | DX02713010 | CsVMV::At5g60200 | 32.9455 | 101.7622 |
| 1 | DX02713011 | CsVMV::At5g60200 | 32.0103 | 98.8734 |
| 1 | DX02713012 | CsVMV::At5g60200 | 34.4701 | 106.4715 |
| 1 | DX02713013 | CsVMV::At5g60200 | 31.181 | 96.312 |
| 1 | DX02714001 | None | 34.4992 | 106.5612 |
| 1 | DX02714002 | None | 31.9208 | 98.5969 |
| 1 | DX02714003 | None | 33.3759 | 103.0917 |
| 1 | DX02714004 | None | 30.4983 | 94.2032 |
| 1 | DX02714005 | None | 32.2863 | 99.726 |
| 1 | DX02714006 | None | 29.4836 | 91.069 |
| 1 | DX02714007 | None | 34.3731 | 106.1718 |
| 1 | DX02714008 | None | 32.5628 | 100.5801 |
| 2 | DX02854001 | CsVMV::At5g60200 | 34.3066 | 109.8032 |
| 2 | DX02854002 | CsVMV::At5g60200 | 31.3106 | 100.2138 |
| 2 | DX02854003 | CsVMV::At5g60200 | 35.2215 | 112.7312 |
| 2 | DX02854004 | CsVMV::At5g60200 | 33.6114 | 107.578 |
| 2 | DX02854005 | CsVMV::At5g60200 | 36.1612 | 115.7391 |
| 2 | DX02854006 | CsVMV::At5g60200 | 33.7712 | 108.0893 |
| 2 | DX02854007 | CsVMV::At5g60200 | 30.2561 | 96.8389 |
| 2 | DX02854008 | CsVMV::At5g60200 | 30.6028 | 97.9485 |
| 2 | DX02854009 | CsVMV::At5g60200 | 31.4406 | 100.6301 |
| 2 | DX02854010 | CsVMV::At5g60200 | 32.2865 | 103.3376 |
| 2 | DX02854011 | CsVMV::At5g60200 | 31.1636 | 99.7436 |
| 2 | DX02854012 | CsVMV::At5g60200 | 33.6948 | 107.8448 |
| 2 | DX02854013 | CsVMV::At5g60200 | 32.9067 | 105.3226 |
| 2 | DX02854014 | CsVMV::At5g60200 | 34.3927 | 110.0786 |
| 2 | DX02854015 | CsVMV::At5g60200 | 34.9508 | 111.8648 |
| 2 | DX02853001 | None | 33.4729 | 107.1347 |
| 2 | DX02853002 | None | 32.1806 | 102.9984 |
| 2 | DX02853003 | None | 32.9593 | 105.4908 |
| 2 | DX02853004 | None | 29.0012 | 92.8224 |
| 2 | DX02853005 | None | 29.8555 | 95.5567 |
| 2 | DX02853006 | None | 32.8813 | 105.2413 |
| 2 | DX02853007 | None | 30.02 | 96.0831 |
| 2 | DX02853008 | None | 29.5792 | 94.6725 |

Example 4

Analysis of *Arabidopsis* HIO41 Sequence

The amino acid sequence encoded by the HIO41 nucleic acid sequence of SEQ ID NO:1 was determined and is presented in SEQ ID NO:2. Sequence analyses were performed with BLAST (Altschul et al., 1990, J. Mol. Biol. 215:403-410), PFAM (Bateman et al., 1999, Nucleic Acids Res 27:260-262), and PSORT (Nakai K, and Horton P, 1999, Trends Biochem Sci 24:34-6) and/or CLUSTAL (Thompson J D et al., 1994, Nucleic Acids Res 22:4673-4680).

TBLASTN against ESTs:

The candidate gene At5g60200 is supported by full-length cDNA GI:29028843. There are many ESTs from diverse plant species showing similarity to At5g60200. Where possible, ESTs contigs of each species were made. The top hit for each of the following species are listed below and included in the "Orthologue Table": *Triticum aestivum, Gossypium hirsutum, Zea mays, Glycine max, Mentha x piperita, Populus tremula, Oryza sativa, Lycopersicon esculentum, Solanum tuberosum,* and *Beta vulgaris.*

1. Wheat ESTs with the following GenBank Ids: gi|20434933; gi|20436734; gi|21557855; gi|22029254; gi|25436506; gi|25448884; gi|3790263 gi|20433676; gi|20432009; gi|9357722, were contigged as SEQ. ID. No. 3.

2. Maize ESTs with the following GenBank Ids: gi|21216133; gi|2393774; gi|511365; gi|6020953; gi|5936836; gi|5123994; gi|12972595 were contigged as SEQ. ID. No. 4.

3. Soybean ESTs with the following GenBank Ids: gi|13311886; gi|18731872; gi|22540117 were contigged as SEQ. ID. No. 5.

4. Poplar ESTs with the following GenBank IDS: gi|24076240; gi|24102174 were contigged as SEQ. ID. No. 6

5. Rice ESTs with the following GenBank Ids: gi|4996641; gi|2428618; gi|4996641 were contigged as SEQ. ID. No. 7

6. Tomato ESTs with the following GenBank Ids: gi|4384148; gi|12634660; gi|12632560; gi|4382344; gi|12635824; gi|7409548 were contigged as SEQ. ID. No. 8

7. Potato ESTs with the following GenBank Ids: gi|21924448; gi|14641934; gi|17076590; gi|21924449 were contigged as SEQ. ID. No. 9

8. One EST contig from sugar beet
gi|26113822 BQ584245 E011860-024-003-D21-SP6 MPIZ-ADIS-024-inflorescence Beta vulgaris cDNA clone 024-003-D215-P.

BLASTP against Amino acids:

The protein At5g60200 has a high degree of homology to a large number of plant proteins and lower degree of homology to proteins from plants, animals and bacteria. The top 12 BLAST hits are listed below and are included in Table 1 below.

1. At5g60200 itself (several redundant entries)
>GI:18424330 Dof-type zinc finger domain-containing protein [*Arabidopsis thaliana*]>gi|29028844| At5g60200 [*Arabidopsis thaliana*]
Length=257
Score=1308 (465.5 bits), Expect=8.6e-133, P=8.6e-133
Identities=239/257 (92%), Positives=239/257 (92%)

2. At3g45610 from *Arabidopsis* (several redundant entries)
>GI:15231189 Dof-type zinc finger domain-containing protein [*Arabidopsis thaliana*]>pir||T47501 dof6 zinc finger protein—*Arabidopsis thaliana*>emb|CAB75490.1| dof6 zinc finger protein [*Arabidopsis thaliana*]>gi|17065414| dof6 zinc finger protein [*Arabidopsis thaliana*] >gi|30023718| At3g45610 [*Arabidopsis thaliana*]
Length=245
Score=660 (237.4 bits), Expect=4.0e-64, P=4.0e-64
Identities=144/253 (56%), Positives=167/253 (66%)

3. At5g62940 from *Arabidopsis*
>GI:15242003 Dof-type zinc finger domain-containing protein [*Arabidopsis thaliana*]
Length=372
Score=302 (111.4 bits), Expect=2.2e-32, Sum P(3)=2.2e-32
Identities=51/62 (82%), Positives=57/62 (91%)

4. At2g28510 from *Arabidopsis* (several redundant entries)
>GI:18401763| Dof-type zinc finger domain-containing protein [*Arabidopsis thaliana*]>gi|17979383| putative DOF zinc finger protein [*Arabidopsis thaliana*]>gi|20197881| putative DOF zinc finger protein [*Arabidopsis thaliana*] >gi|25054955| putative DOF zinc finger protein [*Arabidopsis thaliana*]
Length=288
Score=343 (125.8 bits), Expect=1.6e-30, P=1.6e-30
Identities=81/200 (40%), Positives=108/200 (54%)

5. At3g61850 from *Arabidopsis* (2 redundant entries)
>GI:18401763 Dof zinc finger protein DAG1/Dof affecting germination 1 (DAG1)/transcription factor BBFa (BBFA) [*Arabidopsis thaliana*]>gi|26449798| putative transcription factor BBFa [*Arabidopsis thaliana*]
Length=284
Score=298 (110.0 bits), Expect=6.6e-29, Sum P(2)=6.6e-29
Identities=60/119 (50%), Positives=77/119 (64%)

The following entries are alternatively spliced versions of the gene At3g61850
>GI:15228621 Dof zinc finger protein DAG1/Dof affecting germination 1 (DAG1)/transcription factor BBFa (BBFA) [*Arabidopsis thaliana*]>gi|24211608 DOF zinc finger protein DAG1 (Dof affecting germination 1)(Transcription factor BBFa) (AtBBFa)(rolB domain B factor a)>pir||T47977 transcription factor BBFa [similarity]-*Arabidopsis thaliana*>emb|CAB40190.1| DNA-binding protein [*Arabidopsis thaliana*]>emb|CAB71892.1| transcription factor BBFa [*Arabidopsis thaliana*]>emb|CAA66600.2| Zn finger protein [*Arabidopsis thaliana*]
Length=296
Score=298 (110.0 bits), Expect=6.6e-29, Sum P(2)=6.6e-29
Identities=60/119 (50%), Positives=77/119 (64%)

6. At1g64620 from *Arabidopsis* (several redundant entries)
>GI:18408092 Dof-type zinc finger domain-containing protein [*Arabidopsis thaliana*]>gi|28393305| putative Dof zinc finger protein [*Arabidopsis thaliana*]>gi|28827674| putative Dof zinc finger protein [*Arabidopsis thaliana*]
Length=352
Score=321 (118.1 bits), Expect=3.3e-28, P=3.3e-28
Identities=72/150 (48%), Positives=82/150 (54%)

7. At4g00940 from *Arabidopsis*
>GI:18408092 Dof-type zinc finger domain-containing protein [*Arabidopsis thaliana*]
Length=294
Score=310 (114.2 bits), Expect=4.9e-27, P=4.9e-27
Identities=66142 (46%), Positives=82142 (57%)

8. OsDof-7 from rice (several redundant entries, nomenclature according reference [1])
>gi|19387252 putative zinc-finger protein [*Oryza sativa* (japonica cultivar-group)]>gi|41053112| Dof-like protein 34 [*Oryza sativa* (japonica cultivar-group)] gi|41053157| Dof-like protein 34 [*Oryza sativa* (japonica cultivar-group)]
Length=299
Score=307 (113.1 bits), Expect=1.0e-26, P=1.0e-26
Identities=58/95 (61%), Positives=68/95 (71%)

9. At4g24060 from *Arabidopsis* (2 redundant entries)
>GI:18416267 Dof-type zinc finger domain-containing protein [*Arabidopsis thaliana*]>gi|2262110| zinc finger protein isolog [*Arabidopsis thaliana*]
Length=342
Score=304 (112.1 bits), Expect=2.1e-26, P=2.1e-26
Identities=54/80 (67%), Positives=60/80 (75%)

10. At2g46590 from *Arabidopsis* (several redundant entries)
>GI:30690446 Dof zinc finger protein DAG2/Dof affecting germination 2 (DAG2) [*Arabidopsis thaliana*] >gi|2805 8739| putative DOF zinc finger protein [*Arabidopsis thaliana*]>gi|31711850| At2g46590 [*Arabidopsis thaliana*]
Length=357
Score=299 (110.3 bits), Expect=7.2e-26, P=7.2e-26
Identities=68/165 (41%), Positives=87/165 (52%)

11. At1g21340 from *Arabidopsis*
>GI:15218970 Dof-type zinc finger domain-containing protein [*Arabidopsis thaliana*]
Length=260
Score=292 (107.8 bits), Expect=4.0e-25, P=4.0e-25
Identities=64/142 (45%), Positives=79/142 (55%)

12. At3g52440 from *Arabidopsis*
>GI:15231220 Dof-type zinc finger domain-containing protein [*Arabidopsis thaliana*]>pir||T08455 hypothetical protein F22O6.180—*Arabidopsis thaliana* >emb|CAB43436.1| putative DNA-binding protein [*Arabidopsis thaliana*]
Length=247
Score=287 (106.1 bits), Expect=1.3e-24, P=1.3e-24
Identities=46/57 (80%), Positives=52/57 (91%)

TABLE 1

| Ortholog Gene Name | Species | GI # | % ID to HIO41 | Score(s) (BLAST, Clustal, etc.) |
|---|---|---|---|---|
| A putative zinc-finger protein from rice | Oryza sativa (japonica cultivar-group) | gi\|19387252 gi\|41053112 | Length = 299 Identities = 58/95 (61%), Positives = 68/95 (71%) | BLASTP Score = 307 (113.1 bits), Expect = 1.0e − 26, P = 1.0e − 26 |
| One EST contig from wheat | Triticum aestivum | gi\|20434933 gi\|20436734 gi\|21557855 gi\|22029254 gi\|25436506 gi\|25448884 gi\|3790263 gi\|20433676 gi\|20432009 gi\|9357722 consensus: SEQ. ID. No. 3 | Length = 1405 Plus Strand HSPs: Identities = 80/212 (37%), Positives = 107/212 (50%), Frame = +2 | TBLASTN Score = 308 (113.5 bits), Expect = 2.0e − 27, P = 2.0e − 27 |
| One EST contig from maize | Zea mays | gi\|21216133 gi\|2393774 gi\|511365 gi\|6020953 gi\|5936836 gi\|5123994 gi\|12972595 consensus: SEQ. ID. No. 4 | Length = 1218 Plus Strand Hsps: Identities = 52/62 (83%), Positives = 58/62 (93%), Frame = +1 | TBLASTN Score = 317 (116.6 bits), Expect = 6.7e − 29, P = 6.7e − 29 |
| One EST contig from soybean | Glycine max | gi\|13311886 gi\|18731872 gi\|22540117 consensus: SEQ. ID. No. 5 | Length = 604 Plus Strand Hsps: Identities = 77/142 (54%), Positives = 89/142 (62%), Frame = +1 | TBLASTN Score = 363 (132.8 bits), Expect = 2.8e − 33, P = 2.8e − 33 |
| One EST contig from poplars | Populus tremula | gi\|24076240 gi\|24102174 consensus: SEQ. ID. No. 6 | Length = 749 Plus Strand Hsps: Identities = 63/129 (48%), Positives = 78/129 (60%), Frame = +2 | TBLASTN Score = 318 (117.0 bits), Expect = 5.4e − 29, P = 5.4e − 29 |
| One EST contig from rice | Oryza sativa | gi\|4996641 gi\|2428618 gi\|4996641 consensus: SEQ. ID. No. 7 | Length = 1550 Plus Strand Hsps: Identities = 62/109 (56%), Positives = 70/109 (64%), Frame = +3 | TBLASTN Score = 301 (111.0 bits), Expect = 2.2e − 29, Sum P(2) = 2.2e − 29 |
| One EST contig from tomato | Lycopersicon esculentum | gi\|4384148 gi\|12634660 gi\|12632560 gi\|4382344 gi\|12635824 gi\|7409548 consensus: SEQ. ID. No. 8 | Length = 873 Plus Strand HSPs: Identities = 59/76 (77%), Positives = 63/76 (82%), Frame = +2 | TBLASTN Score = 337 (123.7 bits), Expect = 4.5e − 41, Sum P(3) = 4.5e − 41 |
| One EST contig from potato | Solanum tuberosum | gi\|21924448 gi\|14641934 gi\|17076590 gi\|21924449 consensus: SEQ. ID. No. 9 | Length = 1322 Plus Strand HSPs: Identities = 83/167 (49%), Positives = 99/167 (59%), Frame = +3 | TBLASTN Score = 367 (134.2 bits), Expect = 2.2e − 34, P = 2.2e − 34 |
| One EST contig from sugar beet | Beta vulgaris | gi\|26113822 | Length = 600 Plus Strand HSPs: Identities = 44/76 (57%), Positives = 60/76 (78%), Frame = +2 | TBLASTN Score = 269 (99.8 bits), Expect = 4.7e − 24, P = 4.7e − 24 |

| | Closest Arabidopsis homologs: | | | |
|---|---|---|---|---|
| At3g45610 | Arabidopsis thaliana | >gi\|15231189<br>>gi\|17065414<br>>gi\|30023718 | Length = 245<br>Identities = 144/253<br>(56%), Positives = 167/253 (66%) | BLASTP<br>Score =<br>660 (237.4 bits),<br>Expect = 4.0e−64, P =<br>4.0e−64 |
| At5g62940 | Arabidopsis thaliana | >gi\|15242003 | Length = 372<br>Identities = 51/62<br>(82%), Positives = 57/62 (91%) | BLASTP<br>Score =<br>302 (111.4 bits),<br>Expect = 2.2e−32,<br>Sum P(3) = 2.2e−32 |
| At2g28510 | Arabidopsis thaliana | >gi\|18401763<br>>gi\|17979383<br>>gi\|20197881<br>>gi\|25054955 | Length = 288<br>Identities = 81/200<br>(40%), Positives = 108/200 (54%) | BLASTP<br>Score =<br>343 (125.8 bits),<br>Expect = 1.6e−30, P =<br>1.6e−30 |
| At3g61850.2 | Arabidopsis thaliana | >gi\|30695501<br>>gi\|26449798 | Length = 284<br>Identities = 60/119<br>(50%), Positives = 77/119 (64%) | BLASTP<br>Score =<br>298 (110.0 bits),<br>Expect = 6.6e−29,<br>Sum P(2) = 6.6e−29 |
| At3g61850.1 | Arabidopsis thaliana | >gi\|15228621<br>>gi\|24211608 | Length = 296<br>Identities = 60/119<br>(50%), Positives = 77/119 (64%) | BLASTP<br>Score =<br>298 (110.0 bits),<br>Expect = 6.6e−29,<br>Sum P(2) = 6.6e−29 |
| At1g64620 | Arabidopsis thaliana | >gi\|18408092<br>>gi\|28393305<br>>gi\|28827674 | Length = 352<br>Identities = 72/150<br>(48%), Positives = 82/150 (54%) | BLASTP<br>Score =<br>321 (118.1 bits),<br>Expect = 3.3e−28, P =<br>3.3e−28 |
| At4g00940 | Arabidopsis thaliana | >gi\|22328198 | Length = 294<br>Identities = 66/142<br>(46%), Positives = 82/142 (57%) | BLASTP<br>Score =<br>310 (114.2 bits),<br>Expect = 4.9e−27, P =<br>4.9e−27 |
| At4g24060 | Arabidopsis thaliana | >gi\|18416267<br>>gi\|2262110 | Length = 342<br>Identities = 54/80<br>(67%), Positives = 60/80 (75%) | BLASTP<br>Score =<br>304 (112.1 bits),<br>Expect = 2.1e−26, P =<br>2.1e−26 |
| At2g46590 | Arabidopsis thaliana | >gi\|30690446<br>>gi\|28058739<br>>gi\|31711850 | Length = 357<br>Identities = 68/165<br>(41%), Positives = 87/165 (52%) | BLASTP<br>Score =<br>299 (110.3 bits),<br>Expect = 7.2e−26, P =<br>7.2e−26 |
| At1g21340 | Arabidopsis thaliana | >gi\|15218970 | Length = 260<br>Identities = 64/142<br>(45%), Positives = 79/142 (55%) | BLASTP<br>Score =<br>292 (107.8 bits),<br>Expect = 4.0e−25, P =<br>4.0e−25 |
| At3g52440 | Arabidopsis thaliana | >gi\|15231220 | Length = 247<br>Identities = 46/57<br>(80%), Positives = 52/57 (91%) | BLASTP<br>Score =<br>287 (106.1 bits),<br>Expect = 1.3e−24, P =<br>1.3e−24 |

At5g60200 is a non-secretory protein that lacks transmembrane domain (predicted by TMHMM) and signal peptide (predicted by SignalP). The fact that At5g60200 is a member of the plant-specific Dof (DNA binding one finger) family of transcription factors, At5g60200 is likely to be a nuclear protein. In this context, it should be noted that At5g60200 is likely to be a nuclear or cytoplasmic protein based on Psort2 analysis (40% nuclear, 40% cytoplasmic, 8% cytoskeletal, 8% mitochondrial by Psort2). Pfam analysis showed that At5g60200 contains one Dof domain (PF02701). The Dof domain is a plant-specific zinc finger DNA-binding domain, that shows resemblance to the Cys2 zinc finger, although it has a longer putative loop where an extra Cys residue is conserved (Esaka et al., 1998). Phylogenetic analysis of the Dof gene family from rice and *Arabidopsis* showed that *Arabidopsis* Dof genes are divided into four groups (Lijavetzky et al., 2003). At5g60200 is a member of the C1+c1 subfamily of Dof transcription factors. Dof protein binds DNA in a sequence specific manner (Yanagisawa et al., 1999). Dof proteins have been reported to have diverse functions in plants such as seed storage protein synthesis in developing endosperm (Vicente-Carbajosa et al., 1997 and Mena et al., 1998), light regulation of genes involved in carbohydrate metabolism (Yanagisawa et al., 1998), plant defense mechanisms (Chen et al., 1996), seed germination (Papi et al., (2000; Papi et al., 2002; and Gualberti et al., 2002), gibberellin response in post-germinating aleurone (Mena et al., 2002 and Washio, K., 2001), auxin response (Kisu et al., 1998; Kisu et al., 1997 and Baumann et al. 1999) and stomata guard cell specific gene regulation (Plesch et al., 2001). In view of these results, At5g60200 is predicted to play a key role in regulating gene expression by binding to DNA and therefore functions as a transcription factor.

| Model | Domain | seq-f* | seq-t | hmm-f | hmm-t | score | E-value |
|---|---|---|---|---|---|---|---|
| zf-Dof | 1/1 | 50 | 112 .. | 1 | 63 [] | 139.1 | 1.6e−38 |

*Seq-f refers to "sequence-from" and seq-t refers to "sequence-to." The two periods following the seq-t number indicate that the matching region was within the sequence and did not extend to either end. The two brackets indicate that the match spanned the entire length of the profile HMM. hmm-f and hmm-t refer to the beginning and ending coordinates of the matching portion of the profile HMM.

Example 5

Transformed explants of rapeseed, soy, corn, sunflower, cotton, cocoa, safflower, oil palm, coconut palm, flax, castor and peanut are obtained through *Agrobacterium tumefaciens*-mediated transformation or microparticle bombardment. Plants are regenerated from transformed tissue. The greenhouse grown plants are then analyzed for the gene of interest expression levels as well as oil levels.

Example 6

This example provides analytical procedures to determine oil and protein content, mass differences, amino acid composition, free amino acid levels, and micronutrient content of transgenic maize plants.

Oil levels (on a mass basis and as a percent of tissue weight) of first generation single corn kernels and dissected germ and endosperm are determined by low-resolution $^1$H nuclear magnetic resonance (NMR)(Tiwari et al., *JAOCS*, 51:104-109 (1974); or Rubel, *JAOCS*, 71:1057-1062 (1994)), whereby NMR relaxation times of single kernel samples are measured, and oil levels are calculated based on regression analysis using a standard curve generated from analysis of corn kernels with varying oil levels as determined gravimetrically following accelerated solvent extraction. One-way analysis of variance and the Student's T-test (JMP, version 4.04, SAS Institute Inc., Cary, N.C., USA) are performed to identify significant differences between transgenic and non-transgenic kernels as determined by transgene-specific PCR.

Oil levels and protein levels in second generation seed are determined by NIT spectroscopy, whereby NIT spectra of pooled seed samples harvested from individual plants are measured, and oil and protein levels are calculated based on regression analysis using a standard curve generated from analysis of corn kernels with varying oil or protein levels, as determined gravimetrically following accelerated solvent extraction or elemental (%N) analysis, respectively. One-way analysis of variance and the Student's T-test are performed to identify significant differences in oil (% kernel weight) and protein (% kernel weight) between seed from marker positive and marker negative plants.

The levels of free amino acids are analyzed from each of the transgenic events using the following procedure. Seeds from each of the transgenic plants are crushed individually into a fine powder and approximately 50 mg of the resulting powder is transferred to a pre-weighed centrifuge tube. The exact sample weight is recorded and 1.0 ml of 5% trichloroacetic acid is added to each sample tube. The samples are mixed at room temperature by vortex and then centrifuged for 15 minutes at 14,000 rpm on an Eppendorf microcentrifuge (Model 5415C, Brinkmann Instrument, Westbury, N.Y.). An aliquot of the supernatant is removed and analyzed by HPLC (Agilent 1100) using the procedure set forth in Agilent Technical Publication "Amino Acid Analysis Using the Zorbax Eclipse-AAA Columns and the Agilent 1100 HPLC," Mar. 17, 2000.

Quantitative determination of total amino acids from corn is performed by the following method. Kernels are ground and approximately 60 mg of the resulting meal is acid-hydrolyzed using 6 N HCl under reflux at 100° C. for 24 hrs. Samples are dried and reconstituted in 0.1 N HCl followed by precolumn derivatization with α-phthalaldehyde (OPA0 for HPLC analysis. The amino acids are separated by a reverse-phase Zorbax Eclipse XDB-C18 HPLC column on an Agilent 1100 HPLC (Agilent, Palo Alto, Calif.). The amino acids are detected by fluorescence. Cysteine, proline, asparagine, glutamine, and tryptophan are not included in this amino acid screen (Henderson et al., "Rapid, Accurate, Sensitive and Reproducible HPLC Analysis of Amino acids, Amino Acid Analysis Using Zorbax Eclipse-AAA Columns and the Agilent 1100 HPLC," Agilent Publication (2000); see, also, "Measurement of Acid-Stable Amino Acids," AACC Method 07-01 (American Association of Cereal Chemists, Approved Methods, 9th edition (LCCC# 95 -75308)). Total tryptophan is measured in corn kernels using an alkaline hydrolysis method as described (Approved Methods of the American Association of Cereal Chemists—10$^{th}$) edition, AACC ed, (2000) 07-20 Measurement of Tryptophan—Alakline Hydrolysis).

Tocopherol and tocotrienol levels in seeds are assayed by methods well-known in the art. Briefly, 10 mg of seed tissue are added to 1 g of microbeads (Biospec Product Inc, Barlesville, Okla.) in a sterile microfuge tube to which 500 µl 1% pyrogallol (Sigma Chemical Co., St. Louis, Mo.)ethanol have been added. The mixture is shaken for 3 minutes in a mini Beadbeater (Biospec) on "fast" speed, then filtered through a 0.2 µm filter into an autosampler tube. The filtered extracts are analyzed by HPLC using a Zorbax silica HPLC column (4.6 mm×250 mm) with a fluorescent detection, an excitation at 290 nm, an emission at 336 nm, and bandpass and slits. Solvent composition and running conditions are as listed below with solvent A as hexane and solvent B as methyl-t-butyl ether. The injection volume is 20 µl, the flow rate is 1.5 ml/minute and the run time is 12 minutes at 40° C. The solvent gradient is 90% solvent A, 10% solvent B for 10 minutes; 25% solvent A, 75% solvent B for 11 minutes; and 90% solvent A, 10% solvent B for 12 minutes. Tocopherol standards in 1% pyrogallol/ethanol are run for comparison (α-tocopherol, γ-tocopherol, β-tocopherol, δ-tocopherol, and tocopherol (tocol)). Standard curves for alpha, beta, delta, and gamma tocopherol are calculated using Chemstation software (Hewlett Packard). Tocotrienol standards in 1% pyrogallol/ethanol are run for comparison (α-tocotrienol, γ-tocotrienol, β-tocotrienol, δ-tocotrienol). Standard curves for α-, β-, δ-, and γ-tocotrienol are calculated using Chemstation software (Hewlett Packard).

Carotenoid levels within transgenic corn kernels are determined by a standard protocol (Craft, *Meth. Enzymol.*, 213:185-205 (1992)). Plastiquinols and phylloquinones are determined by standard protocols (Threlfall et al., *Methods in Enzymology*, XVIII, part C, 369-396 (1971); and Ramadan et al., *Eur. Food Res. Technol.*, 214(6):521-527 (2002)).

REFERENCES

Altschul, S. F. et al., *J. Mol. Biol.* 215:403-410, 1990.
Ausubel F M et al. Current Protocols in Molecular Biology, John Wiley & Sons, New York, N.Y., 1993.
Baldwin D et al., *Cur Opin Plant Biol.* 2(2):96-103, 1999.
Bateman et al., 1999, Nucleic Acids Res 27:260-262.

Baulcombe D, *Arch Virol Suppl* 15:189-201, 1999.
Cannon et al., Plant Molec. Biol. (1990) 15:39-47.
Ch'ng et al., Proc. Natl. Acad. Sci. USA (1989) 86:10006-10010
Christensen S et al., 9$^{th}$ International Conference on *Arabidopsis* Research. Univ. of Wisconsin-Madison, Jun. 24-28, 1998. Abstract 165.
Christou et al., Proc. Natl. Acad. Sci USA (1989) 86:7500-7504.
Clough, S J and Bent, A F, *the Plant Journal* 16(6): 735-743, 1998.
De Block et al., Plant Physiol. (1989) 91:694-701.
Dieffenbach C and Dveksler G (Eds.) PCR Primer: A Laboratory Manual, Cold Spring Harbor Laboratory Press, New York, 1995.
Esaka M. , Kisu Y. , Shimofurutani N., Suzuki M. FEBS Lett. 430: 251-256 (1998)
Everett et al., Bio/Technology (1987) 5:1201
Feldmann et al., Science 243: 1351-1354, 1989.
Focks N and Benning C, Plant Physiol 118:91-101, 1998.
Fridborg I et al., *Plant Cell* 11: 1019-1032, 1999.
Harlow E and Lane D, Antibodies: A Laboratory Manual, Cold Spring Harbor Laboratory Press, 1988, New York.
Harlow E and Lane D, Using Antibodies: A Laboratory Manual, Cold Spring Harbor Laboratory Press, 1999, New York
Hayashi H et al., *Science* 258: 1350-1353, 1992.
Jako et al., Plant Physiol. 2001 June;126(2):861-74
James D W and Dooner H K (1990) Theor Appl Genet 80, 241-245.
Jones J D et al, Transgenic Res 1:285-297 1992.
Kardailsky I et al., *Science* 286: 1962-1965, 1999.
Katavic V et al, Plant Physiol. 1995 May;108(1):399-409
Kline et al., Nature (1987) 327:70.
Kunkel T A et al., *Methods Enzymol.* 204:125-39, 1991.
Lemieux B, et al. 1990, Theor Appl Genet 80, 234-240.
Lijavetzky D. et al. BMC Evolutionary Biology 2003, 3:17-28.
Mena M, et al. Plant J 1998, 16:53-62
Nakamura Y et al, 1999, Nucleic Acids Res 27:292.
Napoli, et al, *Plant Cell* 2:279-289, 1990.
Okuley et al., Plant Cell. 1994 January;6(1):147-58)
Sambrook et al. Molecular Cloning: A Laboratory Manual (Second Edition), Cold Spring Harbor Press, Plainview, New York, 1989.
Schaffer R, et al., *Cell* 93: 1219-1229, 1998.
Sheehy et al., Proc. Natl. Acad. Sci. USA (1988) 85:8805-8809.
Smith, et al., *Nature* 334:724-726, 1988.
Smith et al., Mol. Gen. Genetics (1990) 224:477-481.
Thompson J D et al, 1994, Nucleic Acids Res 22:4673-4680.
van der Krol et al., Biotechniques (1988) 6:958-976.
van der Krol et al., The Plant Cell (1990) 2:291-299.
Van Haaren M J J et al., Plant Mol Bio 21:625-640, 1993.
Verdaguer B et al., Plant Mol Biol 37:1055-1067, 1998.
Vicente_Carbajosa J, et al. Proc Natl Acad Sci USA 1997, 94:7685-90.
Waterhouse, et al., *Proc. Natl. Acad. Sci. USA* 95:13959-13964, 1998.
Weigel D, et al., *Plant Physiology,* 122:1003-1013, 2000.
Wilson K et al., *Plant Cell* 8: 659-671, 1996.
Yadav N S et al. (1993) Plant Physiol 103, 467-476.
Yanagisawa S, Schmidt R J. Plant J 1999, 17:209-14.
Yanagisawa S, Sheen J: Plant Cell 1998, 10:75-89.
Chen W, et al. Plant J 1996, 10:955-66 [PubMed Abstract].
Papi M, et al. Genes Dev 2000, 14:28-33.
Papi M, et al. Plant Physiol 2002, 128:411-7.
Gualberti G, et al. Plant Cell 2002, 14:1253-1263.
Mena M, et al. Plant Physiol 2002, 130:111-119.
Washio K: Biochim Biophys Acta 2001, 1520:54-62.
Kisu Y, et al. Plant Cell Physiol 1998, 39:1054-64.
Kisu Y, et al. Plant Cell Physiol 1997, 38:631-7.
Baumann K, et al. Plant Cell 1999, 11:323-34.
Plesch G, et al. Plant J 2001, 28:455-64.
Verdaguer B, et al., (1996) Plant Mol Biol. 31,1129-1139

---

It is claimed:

1. A method of producing oil comprising:
   introducing into progenitor cells of the plant a plant transformation vector comprising a nucleotide sequence that encodes a HIO41 polypeptide comprising the amino acid sequence set forth as SEQ ID NO:2, or an amino acid sequence having at least 95% sequence identity to the amino acid sequence set forth as SEQ ID NO:2;
   growing the transformed progenitor cells to produce a transgenic plant, wherein said polynucleotide sequence is expressed;
   identifying the transgenic plant that exhibits a high oil phenotype relative to a plant of the same species not comprising the plant transformation vector; and
   recovering oil from said transgenic plant.

2. The method of claim 1, wherein the oil is recovered from a seed of the plant.

3. A method of producing a plant having a high oil phenotype, said method comprising:
   introducing into progenitor cells of the plant a plant transformation vector comprising a nucleotide sequence that encodes a HIO41 polypeptide comprising the amino acid sequence set forth as SEQ ID NO:2, or an amino acid sequence having at least 95% sequence identity to the amino acid sequence set forth as SEQ ID NO:2;
   growing the transformed progenitor cells to produce a transgenic plant, wherein said polynucleotide sequence is expressed; and
   identifying the transgenic plant that exhibits a high oil phenotype relative to a plant of the same species not comprising the plant transformation vector.

4. The method of claim 3, wherein the nucleotide sequence encodes a HIO41 polypeptide having an amino acid sequence having at least 95% sequence identity to the amino acid sequence of SEQ ID NO:2.

5. The method of claim 4, wherein the nucleotide sequence encodes a HIO41 polypeptide having the amino acid sequence set forth as SEQ ID NO:2.

6. The method of claim 5 wherein the nucleotide sequence encodes a HIO41 polypeptide consisting of the amino acid sequence set forth as SEQ ID NO: 2.

* * * * *

SEQUENCE LISTING

```
<160> NUMBER OF SEQ ID NOS: 9

<210> SEQ ID NO 1
<211> LENGTH: 1449
<212> TYPE: DNA
<213> ORGANISM: Arabidopsis thaliana

<400> SEQUENCE: 1
acttttaatt  tctactcata  tccatcattc  tctctgatct  caagaaataa  tctcaaatct      60
cttacactca  tagtcttcaa  gcaacttctc  agattcagct  cttatggatc  atttgttaca     120
acaccaggat  gtttttggga  attataacaa  agcaagagaa  gcaatgggac  tatcatattc     180
atcaaaccca  acaccgttag  ataacgacca  gaagaaacct  tctcctgcaa  cggctgtgac     240
aaggccacag  cctccggagc  tagctctcag  gtgtccacgt  tgcgactcaa  caaacacaaa     300
gttttgttac  tacaacaact  acagtctcac  tcagcctcgc  tacttctgca  aatcatgccg     360
gagatattgg  actaaaggtg  gaactctaag  gaacatcccc  gtgggtggag  gctgccggaa     420
aaacaaacga  tccacatctt  cggctgcaag  aagcctcaga  accactccag  aaccggcgtc     480
ccacgacggg  aaagtcttct  cggcggcagg  ttttaatggg  tatagtaaca  atgaacatat     540
```

-continued

```
tgatctgagc ttagcctttg ccttgctgaa caaacaacat ccggggagtt cttcacagct      600
agggtttcat tcagaactcg gtagctctca tcagtctgac atggaaggta tgtttgggac      660
aagccaacaa aaagagaacg ctacttatgc gtttggtaac gggagcagcg gtttgggtga      720
tccaagcaga gtcttatggg gatttccatg gcagatgaat ggagagagct ttggaatgat      780
gaacatagga ggaggtggtg gtcatgtaga tcagattgat tcaggagag agatgtggac      840 caatatgaac tacattaatt ctggtgcttt aatgtagttc aaaattaaaa ccccaatatt      900
atttgggttt tgatttaggg tttgaatttc atgtttttta atgggagtag aaaagggtgg      960
tagctatttt atgaaatggt taaggaagta tagatatatt agggcttctt caaagagttt     1020
caaacttgca aaatggggtt ggggtagttc ttgttttcga tttctgatct aaattgttga     1080
gtttctttat ttgtatgttc actatgttta aatgaaacat ttcctttgtt gttctaattt     1140
cttaattcat tttttctaaa ttaagtttta cgaaattcaa atggcttctg aatgaacaa      1200 aaaatgaaaa tttatcaat gaagaatag tttaccatag tatggaatgt gtggaataat      1260
ttaccataat ggaattgtgt gttcaaaccc taatctctcc cattgaaacc taatcattat     1320
ttctcctata aaaatctgac atatagaggc ttcttaatgg ctcggttaat aaggttgatg     1380
tttctactta attgatttag tgacgtaaag gatcaatctt ggtaatggta tataatgtca     1440
aataagtat                                                             1449
```

<210> SEQ ID NO 2
<211> LENGTH: 257
<212> TYPE: PRT
<213> ORGANISM: Arabidopsis thaliana

<400> SEQUENCE: 2

```
Met Asp His Leu Leu Gln His Gln Asp Val Phe Gly Asn Tyr Asn Lys
1               5                   10                  15

Ala Arg Glu Ala Met Gly Leu Ser Tyr Ser Ser Asn Pro Thr Pro Leu
            20                  25                  30

Asp Asn Asp Gln Lys Lys Pro Ser Pro Ala Thr Ala Val Thr Arg Pro
        35                  40                  45

Gln Pro Pro Glu Leu Ala Leu Arg Cys Pro Arg Cys Asp Ser Thr Asn
    50                  55                  60

Thr Lys Phe Cys Tyr Tyr Asn Asn Tyr Ser Leu Thr Gln Pro Arg Tyr
65                  70                  75                  80

Phe Cys Lys Ser Cys Arg Arg Tyr Trp Thr Lys Gly Gly Thr Leu Arg
                85                  90                  95

Asn Ile Pro Val Gly Gly Gly Cys Arg Lys Asn Lys Arg Ser Thr Ser
            100                 105                 110

Ser Ala Ala Arg Ser Leu Arg Thr Thr Pro Glu Pro Ala Ser His Asp
        115                 120                 125

Gly Lys Val Phe Ser Ala Ala Gly Phe Asn Gly Tyr Ser Asn Asn Glu
    130                 135                 140

His Ile Asp Leu Ser Leu Ala Phe Ala Leu Leu Asn Lys Gln His Pro
145                 150                 155                 160

Gly Ser Ser Ser Gln Leu Gly Phe His Ser Glu Leu Gly Ser Ser His
                165                 170                 175

Gln Ser Asp Met Glu Gly Met Phe Gly Thr Ser Gln Gln Lys Glu Asn
            180                 185                 190

Ala Thr Tyr Ala Phe Gly Asn Gly Ser Ser Gly Leu Gly Asp Pro Ser
        195                 200                 205
```

```
Arg Val Leu Trp Gly Phe Pro Trp Gln Met Asn Gly Glu Ser Phe Gly
    210                 215                 220

Met Met Asn Ile Gly Gly Gly Gly His Val Asp Gln Ile Asp Ser
225                 230                 235                 240

Gly Arg Glu Met Trp Thr Asn Met Asn Tyr Ile Asn Ser Gly Ala Leu
                245                 250                 255

Met
```

<210> SEQ ID NO 3
<211> LENGTH: 1405
<212> TYPE: DNA
<213> ORGANISM: Artificial Sequence
<220> FEATURE:
<223> OTHER INFORMATION: Chimeric polynucleotide

<400> SEQUENCE: 3

```
ccacgcgtcc gcccacgcgt ccgggcaact tgaccctatc ccatagcact agaccaaaca      60
acacctatac tccatactac ccttcattca cctgatggag gaagtgtttt cgtcaaactc     120
caagagcaag gcaggtcaga tggcggggga ggcgatagcg ggggcggaga agaagcctcg     180
gccaaagcca gagcagaagg tggaatgccc tcggtgcaag tctggcaaca ccaagttctg     240
ctactacaac aactatagta tgtctcagcc ccgctacttc tgcaaggcct gccgccgcta     300
ctggacccat ggtggctccc tccgcaacgt ccccatcggt ggtggctgcc gcaagcccaa     360
gcgctcgggg acctccgacg cccacaagct cggcgtggcc tcctcaccgg aacccacgac     420
tgtcgtgccc ccttcgacct gcacagggat gaactttgcg aacgtcctcc cgacgtttat     480
gtctgttggt tttgagattc aagcagcct  ttccctaacc gcctttgggt catcatcgtc     540
gtccaacacg gcggcgatga tgtcccctgg tgggacgacg tcgtttctag acgtgctaag     600
agggggtgca ggagggcttc ttgatggcag cctcagtcag aacaatggct actactatgg     660
tgggccagcc attggatcag gcaatgggat gctgatgacg ccgccagcgg tgtcatttgg     720
cattccagtt ccgatgcagc agcatggcga tctcgtggtt ggtggaaatg aataggtgc      780
cgcaactgct tcaatatttc aaggggccac tagcgaggaa ggagatgacg gcatgggggg     840
cgtgatgggg ctccaatggc aaccacaggt tggcaatggt ggaggtggtg gtggtgtatc     900
aggaggcgtg catcacctcg ggactgggaa caatgtgacg atgggcaaca gcaacataca     960
caacaacaac aataacgaca gcggcggtga tgacaacaat ggtgggtcat cgagggattg    1020
ctactggatc aacaatggag gatcaaaccc atggcagagc ctcctcaaca gcacctccct    1080
gatgtaagtg caagaagaaa atgggaaatg gaggtcattg aattggtgaa gtgggtcaat    1140
cgttttctta ctagtttcgg cgcttcttct tcttttactt gcttgactta tttcgctcca    1200
tcattttcat gttttgttta agtggggatt gttttgttta tttgagtgaa actccagaca    1260
atgtgtgtca tctgcgatgc ttaattaagt attgtttgtt tcatgacatt agtaattgaa    1320
ggatttatgg tttaagcttt atctaggtga tgttgtagag aatgcatgca cattattctt    1380
agttaagttg tttacccact gatcc                                          1405
```

<210> SEQ ID NO 4
<211> LENGTH: 1218
<212> TYPE: DNA
<213> ORGANISM: Artificial Sequence
<220> FEATURE:
<223> OTHER INFORMATION: Chimeric polynucleotide

<400> SEQUENCE: 4

-continued

```
cttcttccca gcgacaagag aaaggattag aaaaaggaaa gatccatgga catgatctcc        60
ggcagcactg cagcaacatc aacaccccac aacaaccaac aggcggtgat gttgtcatcc       120
cccattataa aggaggaagc tagggaccca aagcagacac gagccatgcc ccaaataggt       180
ggcagtgggg agcgtaagcc gaggccgcaa ctacctgagg cgctcaagtg cccacgctgc       240
gactccaaca acaccaagtt ttgctactac aacaattata gcatgtcaca accacgctac       300
ttttgcaagg cttgccgccg ctattggaca catggtggta ccctccgcaa tgtccccatt       360
ggtggtgggt gtcgcaagaa caaacatgcc tctagatttg tcttgggctc tcacacctca       420
tcgtcctcat ctgctaccta tgcaccatta tccctagca ccaacgctag ctctagcaat        480
atgagcatca acaaacatat gatgatggtg cctaacatga cgatgcctac cccaacgaca       540
atgggcttat tccctaatgt gctcccaaca cttatgccga caggtggagg cggggccttt       600
gacttcacta tggacaacca acatagatca ttgtccttca caccaatgtc tctacctagc       660
caggggccag tgcctatgct ggctgcagga gggagtgagg caacaccgtc tttcctagag       720
atgctgagag gagggatttt tcatggtagt agtagctata acacaagtct cacgatgagt       780
ggtggcaaca atggaatgga caagccattt tcgctgccat catatggtgc aatgtgcaca       840
aatgggttga gtggctcaac cactaatgat gccagacaac tggtggggcc tcagcaggat       900
aacaaggcca tcatgaagag cagtaataac aacaatggtg tatcattgtt gaacctctac       960
tggaacaagc acaacaacaa caacaacaac aacaacaaca caacaacaa caacaacaac       1020 aagggacaat aaggttagtg tgccagaccg tggaagcgtt gctgctataa ataatgcaat      1080
tgggtagtag tacccagtga aatcaggaga gactagtagc ctagggtgca ttttgattta      1140
tttagttttg gtcaagatga caagtcatca tgaatcaccc ttttattca tttgcatgtt      1200 ttgtttttt ttttttt                                                      1218
```

<210> SEQ ID NO 5
<211> LENGTH: 604
<212> TYPE: DNA
<213> ORGANISM: Artificial Sequence
<220> FEATURE:
<223> OTHER INFORMATION: Chimeric polynucleotide

<400> SEQUENCE: 5

```
gaggcttaac tcaggagtgt gcatattttc gttgtatgga tggatccttc tagtggacaa        60
caccagcaaa tgtctagcca gtcattggag aacatgttgg catgttcaaa agcccaccaa       120
gagagaaaac caacgcctca gccagaacaa gctctaaagt gccccagatg tgactccacc       180
aacaccaaat tctgctacta caacaattac agcctttccc agccaaggta cttctgcaag       240
tcatgcagga gatattggac caaaggaggt acacttagga atgtccctgt gggaggaggg       300
tgcaggaaga acaaaaggtc atcatcatca tcttcaacat caaagagagt tcaagatcaa       360
gcattcacac caaatgttaa ccctctcact ggccttcctt cattaatgtc ttatgactcc       420
aatgacctca ctcttgcatt ggcaaggctt caaaagcagt catgtgggca attagggtat       480
gatgatcatg atctttcaat gttggggaac caccacacaa acaccccatg tggtgataat       540
atccttggca tgcatcacca ctcatcatcc tcatccacaa acccagggtt cttggatgcc       600
ctca                                                                    604
```

<210> SEQ ID NO 6
<211> LENGTH: 749
<212> TYPE: DNA
<213> ORGANISM: Artificial Sequence
<220> FEATURE:
<223> OTHER INFORMATION: Chimeric polynucleotide

<400> SEQUENCE: 6

```
ctaagaagaa gaaaagatga ttcaagaact ctttggaggt gctggcttaa ttggcggaga      60
gaggaaaatt cccatcaatg cgaccatttt agatcaaggc gctccttcac catctccttc     120
atcttccaca acgacgacta cttcagctac taattcaaca ccttcagcgc aagagaaatt     180
gagatgccct cgatgcgatt cttcaaacac caagttctgt tactataaca actataacct     240
cactcagcct cgccacttct gcaagacttg tcgccggtat tggactaaag gtggtgcgct     300
tagaaacgtt ccaattggag gtggatgtag aaaaaacaag aacacaagcg tatcggcctc     360
tgttggaaaa tctggcacaa gtaagataaa aactatagca tctgagattg aagatcagg      420
ttttggaaat gggtttgacc acgagctttc atcaagcccc atcttgcggg cttcaccaca     480
gaattctcat atttttgctt tacttagagc cacccaaaac cctaacccta gtacaccatg     540
taattctatt tctgtgaagc aggaggggtt tttgattgga aagcatatga taagagagcc     600
agcagttgaa acagctgctt tgaatgctag aatcctaggc ttggaccctg ttagtcaagc     660
ttcttctctt ggtctttgca gctcttcttg gaaaagcaat cagcaccaac aaaatcgctt     720
cactgttggt gaagctcaaa actcgggga                                        749
```

<210> SEQ ID NO 7
<211> LENGTH: 1550
<212> TYPE: DNA
<213> ORGANISM: Artificial Sequence
<220> FEATURE:
<223> OTHER INFORMATION: Chimeric polynucleotide

<400> SEQUENCE: 7

```
ctgatctgcg ctcgatcctt tctcgaatcg gtgcatgcaa caccggcgac atgtctacaa      60
ttaagatctc tcaccggggg cccggccggg tcgattttgg cttctgctct tcttctggat     120
cttgttgatg tgggtgtttc ttggtcgatc cttcttgttt aatctgcctg tgccttgatc     180
ttggcgcttg cttttcctct gatctatgca cggatcggcc atattcttct cgctctgtgt     240
gtatgtgggg ctagggcta gtgaagccca tggaagagat gctgatgggt gcaaatccaa      300
atcctaatgg gagctcaaat cagccaccgc caccgccgtc ctcggcggcc agcgcccagc     360
ggcctatcgc cccaccggcg gctggagcgg ccgccggcgc gggcgccgcc ggagctgggg     420
ctggcacgga gcgccgcgcg cggccgcaga aggagaaggc gctcaactgc ccgcggtgca     480
actcgacgaa caccaagttc tgctactaca caactacag cctccagcag ccgcgctact     540
tctgcaagac gtgccgccgc tactggacgg agggcggctc gctccgcaac gtccccgtcg     600
gcggcggctc acggaagaac aagcgctcgt cgtcctcggt ggtgccgtcg gcggccgcgt     660
cggcctccac ctccgcggcg gtgtccggct cggtccccgt ggggctggcg gccaagaacc     720
cgaagctgat gcacgaggga gcgcaggacc tcaacctagc gttcccgcac caccacggcc     780
gcgccctgca gccgcggag ttcacggcgt ccccgagctt ggagagcagc agcgtgtgca     840
accccggagg caacctggcg gcggcgaacg gcgccggtgg cagggcagc gtgggcgcgt      900
tctcggcgat ggagttgctg aggagcaccg gctgctacgt tccgctgccg cagatggcgc     960
cgctagggat gccggcggag tacgcagctg cggggttcca tctcggcgag ttccgcatgc    1020
caccgccgcc acagcagcag cagcagcaac aagctcagac cgtgctcggt ttctccctgg    1080
acacgcacgg cgcgggtgca ggcggcggct ccggggtgtt cggcgcgtgc agcgctgggt    1140
```

```
tgcaagagag cgcggcgggc aggttgctgt tccccttcga ggacctgaag ccggtggtga    1200
gcgccgcggc tggcgacgcg aacagcggcg gcgatcatca gtacgaccac ggcaagaacc    1260
aaggtggtgg cggcggcgtc atcggtggcc atgaggcccc aggttctgg aatagcagca     1320 tgatcggcaa cggcagcagc aatggcggcg gcggcggcgg ttcttggtaa ggtggtgcga    1380
gctgctactg cttgcccgcc gccgccatgc atggctcatg catgcacgcg tggtggtcag    1440
cagctagcag catgtggaga tagagaaacg agatagagac aagggggtt aataagcctg     1500 tggtgattag tgttacatat ggcgttttgt ttctcaaaaa aaaaaaaaa                1550

<210> SEQ ID NO 8
<211> LENGTH: 873
<212> TYPE: DNA
<213> ORGANISM: Artificial Sequence
<220> FEATURE:
<223> OTHER INFORMATION: Chimeric polynucleotide

<400> SEQUENCE: 8
ctaatgcttc tctctattca tatctttcaa tctcttctac ttctcttcta acttttatac     60
attaattttg gtttcaaaaa tatctagaaa ctgaagaaaa aaaatattag aaattgagtt    120
gctaactata tacagctgat taatgtgcat aatggatcat catcagcagg aaatgacttc    180
acaaacacta gaaagcatgt tggtttgcgc aaaaccagat caagatcaaa agaagccaag    240
gcctgcagca gcagagcaac aacctcagaa atgtccaaga tgtgactctg ccaacacgaa    300
attctgttac tataacaact acagcctgac tcaaccgcga tacttctgca aatcctgcag    360
aaggtactgg actaaaggag gtacgctgag aaatgttcca gttggtggtg gttgtagaaa    420
aaaacagaaa attatcatca gcaaagcgat caagccaaga taacattagc cctaacagca    480
gtaattcctc aactgatttg agcctagcat tcgccaggct ccagaaacag acaaatgcga    540
tcgatcaaga acaggatacc aacaacaaca tgtcaatgat gtacaatact aacaacgata    600
acactagtac cacctttcta gatgcactaa gaggtggatt tctcgaaaat catcacggat    660
tgtttcaaca caacatgtat aattacgcga acatggggca attggtagag aatggagaaa    720
tgggattgag ttatgatcaa gatcaaatga gtattggtac aatgatgaca acaacgatga    780
agcaagagat gtgcaacgtg gcacgatcaa cagaagtcat gacctgaatg acaacaacaa    840
agtcttgtgg ggatttccat ggcaacaaat gag                                873

<210> SEQ ID NO 9
<211> LENGTH: 1322
<212> TYPE: DNA
<213> ORGANISM: Artificial Sequence
<220> FEATURE:
<223> OTHER INFORMATION: Chimeric polynucleotide

<400> SEQUENCE: 9
ggagagagaa ctagtctcga gttgtttct tttcttaaag cttttgtatt actaaaattc       60
ttctctctat tcatatcatc caatctcttc tactttctt caattttat acattaattt     120 tggtttcaaa atatatccag aaactgaaaa taaaaataaa aattgagttg ctagctacat    180
acagctgatt aatgtgcata atggatcatc agcagcagga aatgtcttca caaacactag    240
aaagcatgtt ggtttgcaca aaaccagatc aagatcaaaa gaagccaagg ccagcagaac    300
aacaacctca gaaatgtcca agatgtgact ctgccaacac aaaattctgt tactacaaca    360
attatagcct cactcagccc agatactttt gcaaatcttg cagaaggtac tggactaaag    420
gaggtacgct cagaaacgtt ccagttggtg gtggttgtag aaaaaacaaa aaattatcat    480
```

```
                                         -continued
caacaacatc agcaaagaga tcaagtcaag ataacattag cccaaacatc agtaatccaa      540
taccttccta tgattcctca actgatttga gtctggcatt cgccaggctc cagaaacaga      600
caaatgcaca tttggagatc gatcaagaac atgacagcaa caacaacaac aacatgtcaa      660
tgatgtacaa tactggcaac aactgtacta gtactacctt tcttgatgca ctaagaggtg      720
gatttctcga aaatgcccca aatcatcatg gattgtttca tcacaacatg tataattacg      780
cgaacatggg gcaattagta gagaatggag aaatgggaat gagctatgat caagatcaaa      840
tgagtattgg tacaagtact acaatgatga caacgatagt gaagcaagag atgtgcaaca      900
tggcacgatc aacagaaggt catgacctga ataacagtaa taacaacaac aaagtcttgt      960
gtggatttcc atggcaacaa atgaatggag atcatcatgt taacaacatg aatacgaatg     1020
attttgaata ttcaactaac aaacaaagtt ggaatggatt tggaggttct tctaattggc     1080
atggacttat taatagccct ttaatgtaga tgtttaatta gaagaagaag aagaaaaggt     1140
agtattttga ttattaattc ttagattaga ctgtttaat ttttaaatta aatatctaag      1200
aattttgtgt ttagatgttt tgattcatct gaattattaa tccctatgtt gttttttgct     1260 tttttggtt tcatgggctg tgtatctttt tagtttgttt gtctaatatt gattgacaaa      1320
tt                                                                   1322
```